United States Patent
Ochs et al.

(10) Patent No.: US 7,174,904 B2
(45) Date of Patent: Feb. 13, 2007

(54) DENTAL FLOSS DEVICE WITH A STACKABLE DENTAL FLOSS HOLDER

(75) Inventors: Harold Ochs, Flemington, NJ (US); Emanuel Morano, Totowa, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 182 days.

(21) Appl. No.: 10/372,516

(22) Filed: Feb. 24, 2003

(65) Prior Publication Data

US 2004/0163666 A1 Aug. 26, 2004

(51) Int. Cl.
*A61C 15/00* (2006.01)

(52) U.S. Cl. .................................... 132/323

(58) Field of Classification Search ........ 132/321–327; 15/145, 176.1, 176.4, 176.5, 176.6; 403/361, 403/371

See application file for complete search history.

(56) References Cited

U.S. PATENT DOCUMENTS

| | | | |
|---|---|---|---|
| 778,388 A | 12/1904 | Warren | |
| 1,111,144 A | 9/1914 | Epstein | |
| 2,187,899 A | 1/1940 | Henne | |
| 2,354,454 A * | 7/1944 | Geffner | 132/323 |
| 3,182,345 A * | 5/1965 | Smith | 15/176.6 |
| 3,892,249 A | 7/1975 | Jones et al. | |
| 4,026,308 A * | 5/1977 | Krivit | 132/323 |
| 4,192,330 A * | 3/1980 | Johnson | 132/323 |
| 5,105,840 A * | 4/1992 | Giacopuzzi | 132/325 |
| 5,170,809 A * | 12/1992 | Imai et al. | 132/322 |
| 5,388,600 A | 2/1995 | Hart | |
| 5,411,041 A | 5/1995 | Ritter | |
| 5,483,982 A * | 1/1996 | Bennett et al. | 132/323 |
| 5,692,531 A * | 12/1997 | Chodorow | 132/323 |
| 5,819,769 A * | 10/1998 | Gutierrez | 132/327 |
| 6,018,838 A | 2/2000 | Nowack | |
| 6,085,760 A * | 7/2000 | Chodorow | 132/323 |
| 6,457,201 B1 | 10/2002 | Sham | |
| 2003/0098037 A1* | 5/2003 | Dougan et al. | 132/323 |

FOREIGN PATENT DOCUMENTS

| | | |
|---|---|---|
| EP | 0 610 227 B1 | 8/1994 |
| JP | 8173243 A | 7/1996 |

OTHER PUBLICATIONS

European Search Report dated Jan. 20, 2005, for corresponding EP application 04250975.2.

* cited by examiner

*Primary Examiner*—Cary E. O'Connor

(57) ABSTRACT

The present invention relates to dental floss holders that are attachable to handles for receiving the dental floss holder in releasable frictional engagement, which dental floss holders receiving a dental floss holder in releasable frictional engagement, include a length of dental floss secured between the distal ends of arms extending from the base of the holder, to stacks of such floss holders, and to packaged stacks of such floss holders.

13 Claims, 5 Drawing Sheets

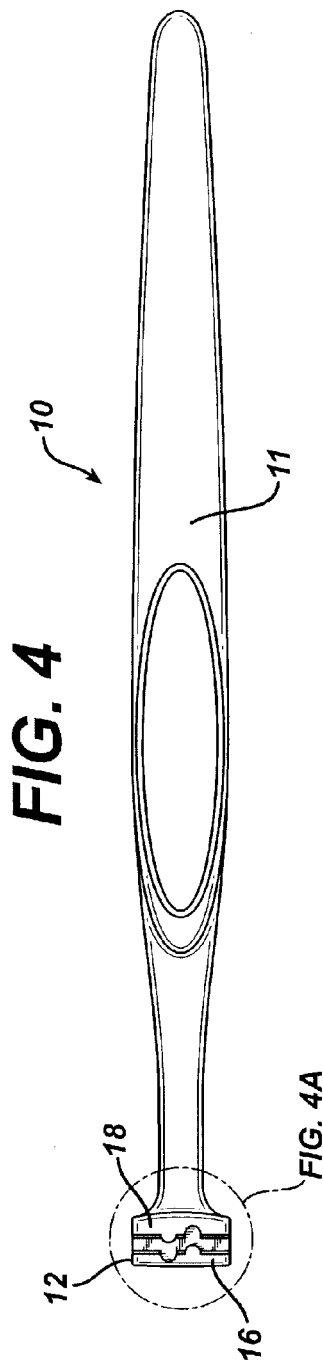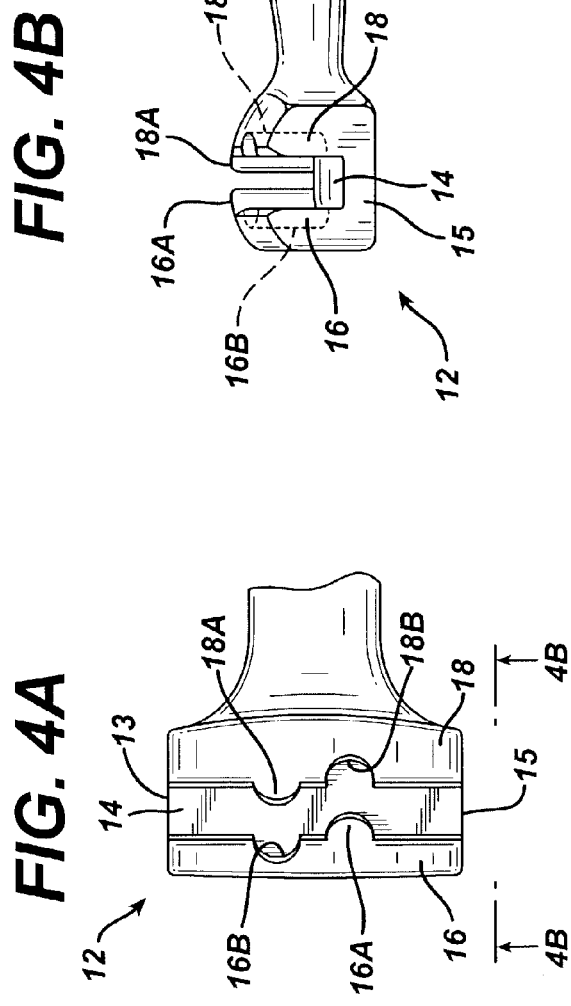

DENTAL FLOSS DEVICE WITH A STACKABLE DENTAL FLOSS HOLDER

BACKGROUND OF THE INVENTION

1. Field of the Invention

This invention relates to a dental floss device including a handle having a head portion, and a stackable dental floss holder. The dental floss holder releasably attaches to the head portion of the handle by releasable engagement means. The releasable engagement means includes indentations and protrusions on both the dental floss holder and the head portion of the handle. The arrangement of the indentations and protrusions on the dental floss holder makes the dental floss holder stackable. Preferably, the dental floss comprises snap fitting means for enhancing the securement of the dental floss holder to the head portion of the handle.

2. Description of the Prior Art

Dental floss devices having removable dental floss holders or cartridges are known in the art. The devices generally include a handle with a head portion designed to receive and hold a dental floss holder. In use, the dental floss holder is attached to the head portion and the floss is inserted between teeth. After a number of teeth have been cleaned with the floss, the dental floss holder is removed and replaced with a new dental floss holder.

Replacement dental floss holders are typically packaged and sold in lots of ten or twenty units. The process for making dental floss holders typically involves injection molding of a plurality of holders simultaneously in a mold into which has been threaded a length of dental floss material. The plurality of formed dental floss holders are connected by a plastic backbone as they come out of the molding step. After being formed and cooled, the dental floss holders are removed from the backbone and sent to packaging. Most dental floss holders are not stackable as a result of which they are cumbersome to handle during post-molding and packaging operations.

A dental floss device comprising a handle and a non-stackable dental floss holder engageable therewith is taught in U.S. Pat. No. 5,483,982, the entire disclosure of which is hereby incorporated by reference.

Non-stackable dental floss holders are more difficult to process and take up more space in a package than a corresponding number of stackable dental floss holders would take. The provision of a stackable dental floss holder would simplify handling during the packaging operation and would reduce packaging costs. Costs for packaging dental floss holders would be reduced where the dental floss holders are stackable and are packaged in stacked form. Therefore, there is a need for a stackable dental floss holder.

SUMMARY OF THE INVENTION

In a first embodiment, the present invention provides a dental floss device comprising a handle having an elongated gripping portion and a head portion, and a dental floss holder which is adapted to be releasably connected to the head portion for subsequent use in flossing the teeth. The dental floss device further comprises releasable engagement means for releasably securing the dental floss holder to the handle during use. The head portion of the handle extends transversely of the longitudinal axis of the gripping portion, as a result of which the handle has a generally T-shaped configuration. The head portion includes a generally U-shaped channel for releasably receiving the dental floss holder. The U-shaped channel comprises a floor and two spaced apart walls. A first of the two walls defining the U-shaped channel comprises at least one protrusion and at least one indentation spaced laterally therefrom. The second of the two walls also comprises at least one protrusion and at least one indentation spaced laterally therefrom. The protrusion on the first of the two walls is located substantially opposite the indentation on the second of the two walls. The indentation on the first of the two walls is located substantially opposite the protrusion on the second of the two walls. The dental floss holder has a base portion and a pair of spaced-apart arms extending from the base portion to accommodate a length of dental floss therebetween. The base portion comprises a pair of lateral sides. Each lateral side comprises at least one protrusion and at least one indentation spaced laterally therefrom. The protrusion on the first lateral side is located substantially opposite the indentation on the second lateral side. The indentation on the first lateral side is located substantially opposite the protrusion on the second lateral side. The protrusions and indentations on the two walls defining the U-shaped channel of the head portion are sized and arranged to receive in frictional engagement the indentations and protrusions on the lateral sides of the base portion of the aforementioned dental floss holder. On assembly, the base of the dental floss holder fits into the transversely extending, generally U-shaped channel of the head portion of the handle.

Preferably, the spaced-apart arms of the dental floss holder also include inwardly extending snap fit projections for engagement with the ends of the head portion of the handle. Such engagement of the snap fit projections with the ends of the head portion enhances the degree of securement of the dental floss holder to the head portion of the handle.

In a second embodiment, the present invention provides a stackable dental floss holder comprising a base portion and a pair of spaced-apart arms extending from the base portion. A length of dental floss is secured between the distal ends of the spaced-apart arms. The base portion comprises a pair of lateral sides. Each lateral side comprises at least one protrusion and at least one indentation spaced laterally therefrom. The protrusion on the first lateral side is located opposite the indentation on the second lateral side. The indentation on the first lateral side is located opposite the protrusion on the second lateral side. Preferably, the spaced-apart arms include snap fit projections for engagement with the ends of the head portion of a handle.

In a third embodiment, the present invention provides a handle comprising an elongated gripping portion and a head portion for releasably receiving a dental floss holder. The head portion of the handle extends transversely of the longitudinal axis of the gripping portion, as a result of which the handle has a generally T-shaped configuration. The head portion includes a generally U-shaped channel for releasably receiving the above-described dental floss holder. The U-shaped channel comprises a floor and two spaced apart walls. A first of the two walls defining the U-shaped channel comprises at least one protrusion and at least one indentation spaced laterally therefrom. The second of the two walls also comprises at least one protrusion and at least one indentation spaced laterally therefrom. The protrusion on the first of the two walls is located substantially opposite the indentation on the second of the two walls. The indentation on the first of the two walls is located substantially opposite the protrusion on the second of the two walls. The protrusions and indentations on the two walls defining the U-shaped channel of the head portion are sized and arranged to receive in frictional engagement the indentations and protrusions on the lateral sides of the base portion of the aforementioned dental floss holder.

The two opposed ends of the head portion receive the aforementioned snap fit projections on the dental floss holder.

BRIEF DESCRIPTION OF THE DRAWINGS

FIG. 4 is a top plan view of a handle for releasably receiving the dental floss holder of FIG. 2;

FIG. 4A is an enlarged view of the circled portion of FIG. 4;

FIG. 4B is an enlarged fragmentary side view taken along view line 4B—4B of FIG. 4A;

DETAILED DESCRIPTION OF PREFERRED EMBODIMENTS

Figure 1:
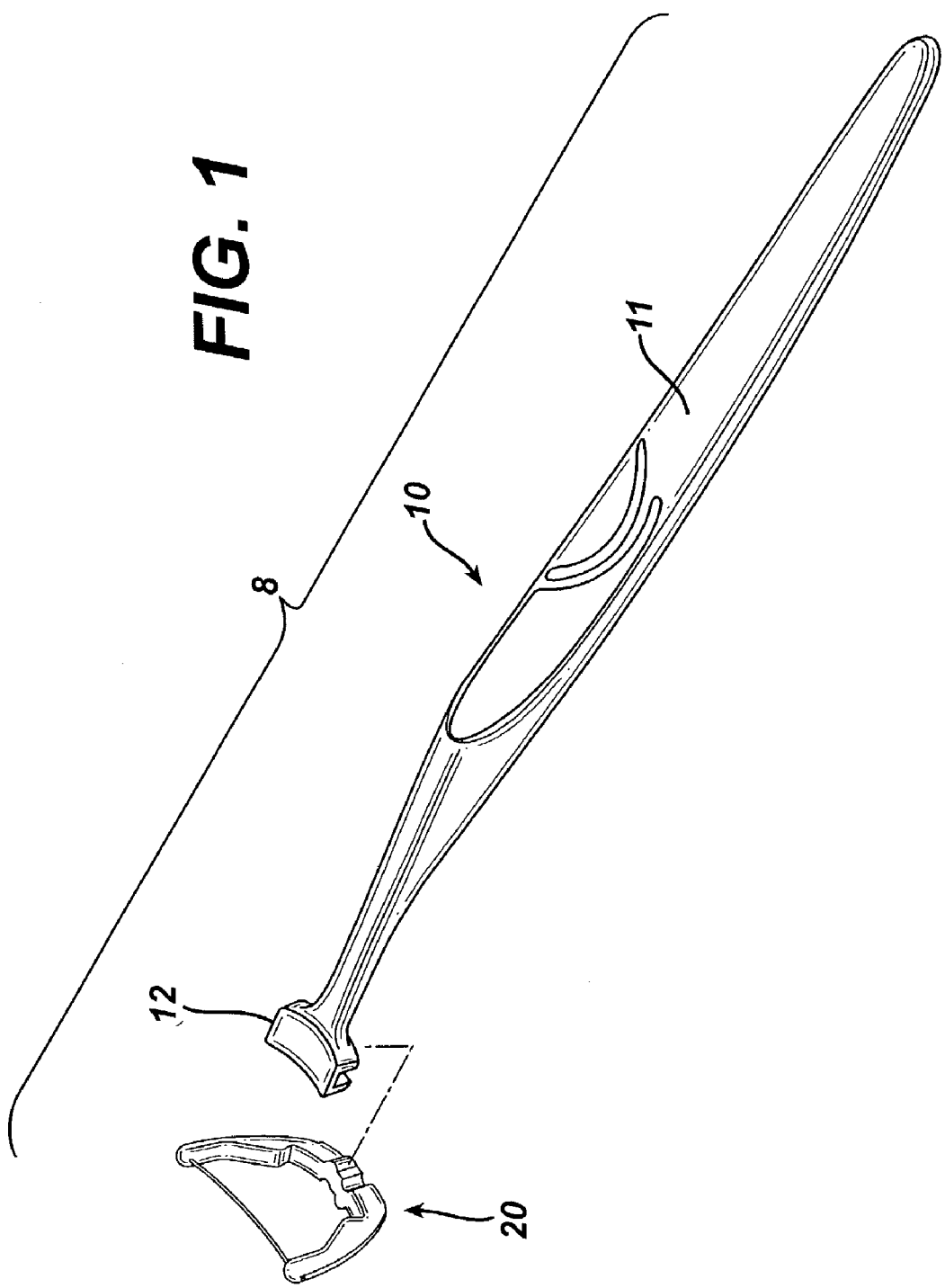
FIG. 1 is an exploded perspective of one embodiment of a dental flossing device in accordance with the present invention.

The handle and stackable dental floss holder comprising the dental floss device of the present invention may be made of any suitable materials known in the art. Suitable materials include polymers such as, but not limited to, acrylics, such as poly methyl methacrylate; polyolefins, such as polyethylene and polypropylene; polyesters, such as polycaprolactone; co-polyesters; polycarbonate; and mixtures thereof.

The handle and dental floss holder may be made of the same material or different materials. Preferably, the handle is made of a material that is harder than the material from which the dental floss holder (exclusive of the dental floss material) is made. In a preferred embodiment, the handle is made from a co-polyester resin and the dental floss holder (exclusive of the dental floss material) is made from a polypropylene resin.

The handle and stackable dental floss holder of the present invention may be made by any suitable process known in the art. Injection molding is preferred.

The dental floss holder retains a length of dental floss for cleaning between teeth. Any dental floss material known in the art may be used in the dental floss holder of the present invention. The dental floss material may be a monofilament or a multi-filament yarn comprising a plurality of such monofilaments.

Dental flosses in the form of a multi-filament yarn are generally circular in cross section and typically have a denier ranging from about 200 to about 1400. The denier of the individual fibers typically ranges from about 1 to about 6, although other deniers may be used in some circumstances if desired.

Psuedo-monofilament yarns may also be used as dental floss material in the present invention. Pseudo-monofilament yarns are made by extruding bi-component fibers comprising a core of one polymer and a sheath of a different polymer, then either partially or totally melting the sheaths of the fibers to bond or fuse the fibers, resulting in a monofilament look and feel. One example of a suitable bicomponent fiber for making pseudo-monofilament yarn is a core of nylon 6 with a sheath of Pebax® brand polyether/amide copolymer. Other materials besides nylon can be used for the core of the bicomponent fibers and other polymeric materials besides polyether/amide copolymer may be used as the sheath material.

Other dental floss materials which may be used in the present invention include, but are not limited to, nylon 6-6, nylon 6, polypropylene, polyethylene, high molecular weight polyethylene, ultra high molecular weight polyethylene, polytetrafluoroethylene, and the like materials. Combinations of such materials may also be used. Ultra high molecular weight polyethylene is a preferred dental floss material.

The individual monofilaments comprising a multifilament dental floss yarn may, if desired, be air entangled. If the yarn is air entangled, the air entanglement nodes may be from about 1.25 cm to about 8.9 cm apart. One type of air entangled yarn is described in U.S. Pat. No. 5,908,039, the disclosure of which is hereby incorporated by reference.

As is known in the art, the dental floss may be twisted. If the dental floss is twisted, it is preferable to have less than 6 turns per 2.54 cm, and more preferably less than 5 turns per 2.54 cm.

As is known in the art, the dental floss may be coated with waxes, flavorants, active ingredients, and the like.

In one process of manufacturing dental floss holders, dental floss is fed through a multi-cavity mold and plastic is then injected into the mold to form the holders. After completion of the injection molding step, the floss may then be cut and tied at the ends.

Alternatively, the ends of the floss material may be heated to form spheres which retain the floss material in place. Manufacturing methods of this type are known in the art and can be used for making dental floss holders of the present invention. See, for example, U.S. Pat. No. 4,006,750; U.S. Pat. Nos. 4,016,892 and 5,086,792, the teachings of all of which are herebyf incorporated by reference.

Figure 2:
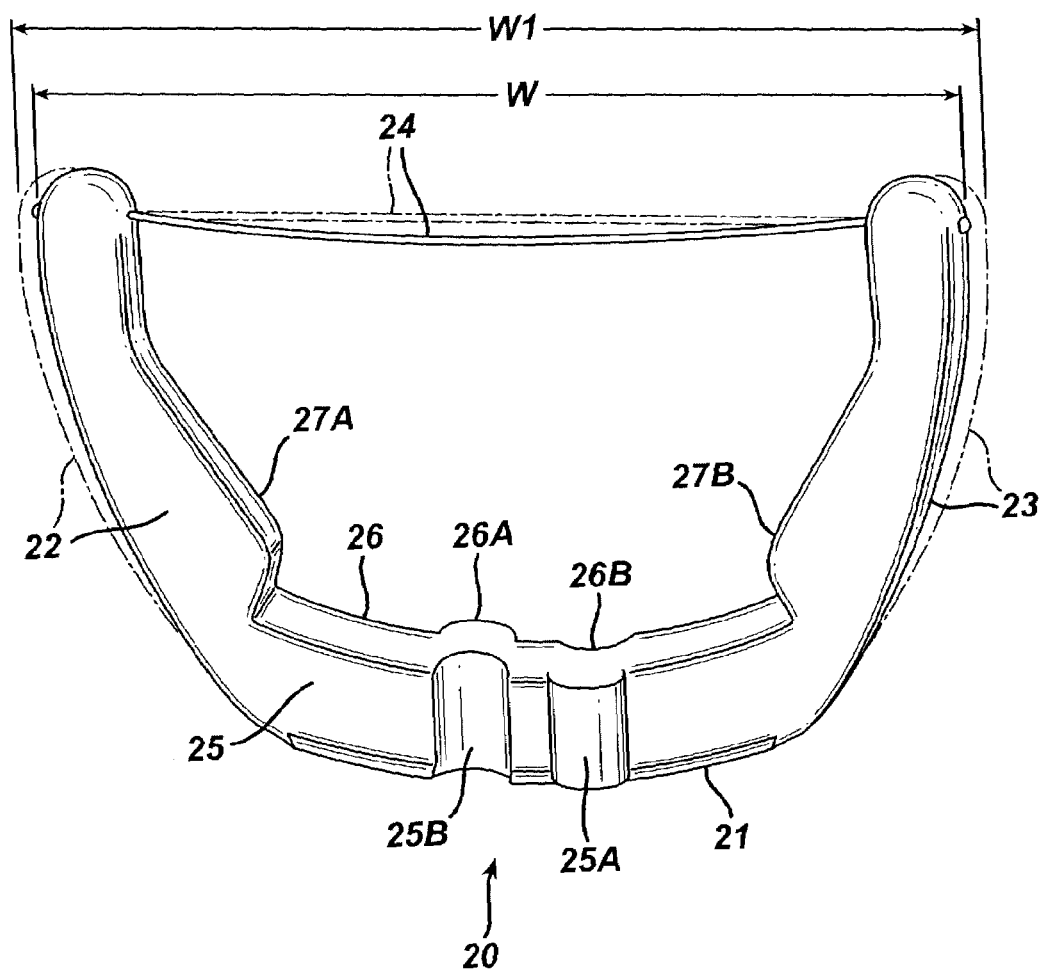
FIG. 2 is a perspective view of one embodiment of a dental floss holder in accordance with the present invention.

The floss in the dental floss holder as made and before insertion into a handle typically has some slack. In use, it is preferred that the dental floss be taut. This is illustrated in FIG. 2, where W illustrates the width of the dental floss holder as made and W1 illustrates the slightly larger width of the dental floss holder when engaged with handle 10 shown in FIG. 1. The relationship between the snap fit projections on the dental floss holder and the ends of the head portion may be arranged to make the floss material taut when the dental floss device is assembled for use. Specifically, the length of the head portion of the handle is sized so that when the dental floss holder is secured in the U-shaped channel of the head portion and the snap fit projections on the arms of the dental floss holder are engaged with the ends of the head portion, the distance between the arms of the dental floss holder is increased, thus making the floss material taut. Typically, this distance ranges from about 0.005 inch to about 0.06 inch, preferably from about 0.01 inch to about 0.02 inch.

Examples are provided below to further illustrate the dental floss holder, the handle and the dental floss device of the present invention. The invention should not be construed as being limited to the specific details set forth herein.

EXAMPLE 1

Handle

A handle in accordance with the teachings of the present invention was made from a commercially available co-polyester resin by an injection molding process. The co-polyester resin had a notched Izod value of 80 joules/m. Referring now to the appended drawings, handle 10 comprises an elongated gripping portion 11 and a head portion 12 at its distal end. Head portion 12 extends transversely of the longitudinal axis of gripping portion 11, as a result of which handle 10 has a generally T-shaped configuration. Head portion 12 includes a generally U-shaped channel (best seen in FIGS. 4A and 4B) for releasably receiving a dental floss holder of the type described hereinabove and in Example 2. The U-shaped channel comprises a convex floor 14 and two spaced apart walls, 16 and 18. First wall 16 comprises a protrusion 16A and an indentation 16B spaced laterally therefrom as shown in FIG. 4A. Second wall 18 defining the U-shaped channel comprises a protrusion 18A and an indentation 18B spaced laterally therefrom. Protrusion 16A on first wall 16 is located substantially opposite indentation 18B in second wall 18. Indentation 16B on first wall 16 is located substantially opposite protrusion 18A on second wall 18. Protrusions 16A,18A and indentations 16B, 18B on walls 16,18 are sized and arranged to receive, in releasable frictional engagement, mating indentations and protrusions on lateral sides 25,26 of base portion 21 of the aforementioned dental floss holder 20. See also Example 2 hereinafter. Sides 13, 15 of head portion 12 engage snap fit projections 27A,27B of dental floss holder 20 when the dental floss device is assembled and ready for use.

EXAMPLE 2

Stackable Dental Floss Holder

A stackable dental floss holder in accordance with the teachings of the present invention was made from a commercially available polypropylene resin by an injection molding process of the kind mentioned earlier herein. The polypropylene resin had a notched Izod value of 30 joules/m. A multifilament, ultra high molecular weight, polyethylene yarn (400 denier, approximately three turns per inch and a denier per filament of about 1.9) was used as the dental floss material. As is seen in FIG. 2, stackable dental floss holder 20 comprises a base portion 21 and a pair of spaced-apart arms 22 and 23 extending from the base portion to accommodate a length of dental floss 24 therebetween. Base portion 21 comprises a pair of lateral sides 25,26. Lateral side 25 comprises a protrusion 25A and an indentation 25B spaced laterally therefrom. Protrusion 25A on first lateral side 25 is located substantially opposite indentation 26B on second lateral side 26. The indentation 25B on first lateral side 25 is located substantially opposite protrusion 26A on second lateral side 26. Preferably, the spaced-apart arms include snap fit projections 27A,27B for engagement with ends 13,15 of head portion 12 of handle 10. This engagement can be best seen in FIG. 3A, where snap fit projections 27A,27B are engaged with the respective corners of sides 13,15 of head portion 12. Dental floss 24 is shown in its slack configuration and in its tautened configuration (dot-and-dash lines) in FIG. 2.

EXAMPLE 3

Dental Flossing Device

Figure 3:
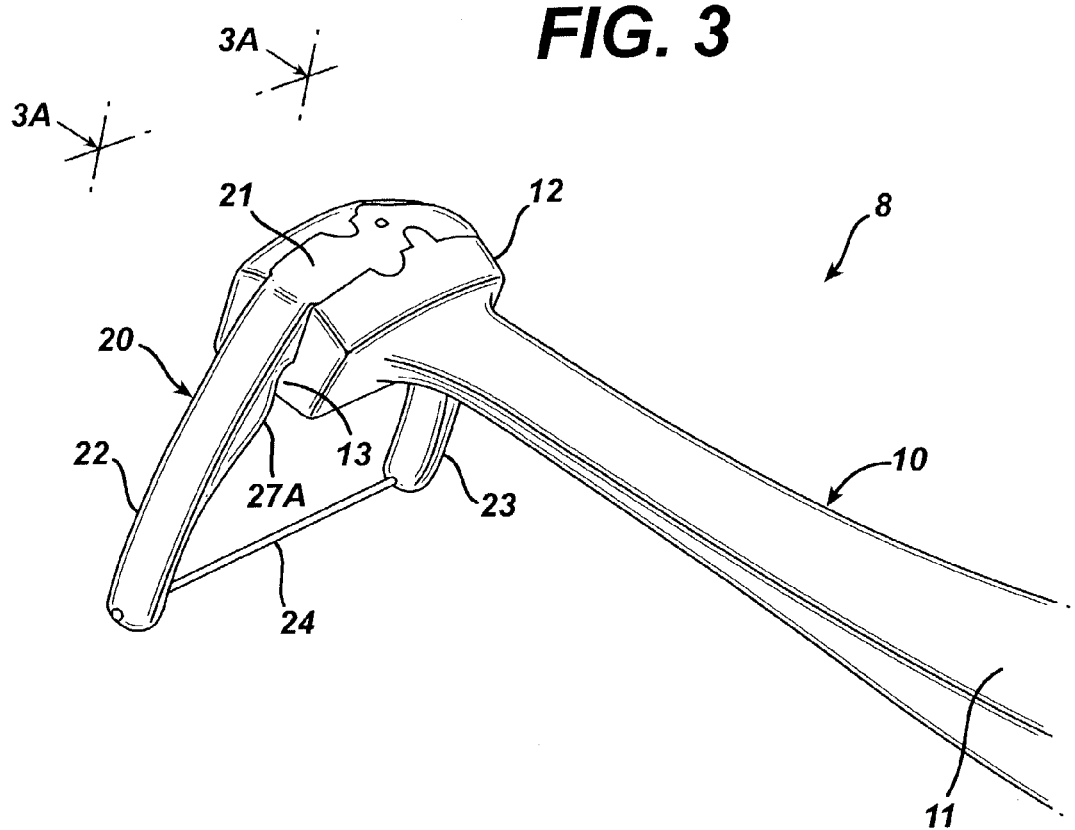
FIG. 3 is a view showing the dental floss holder of FIG. 2 in releasable engagement with the handle shown in FIG. 4.
Figure 3A:
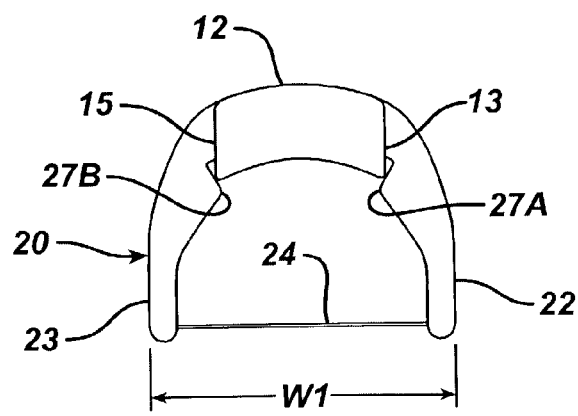
FIG. 3A is a view taken along view line 3A—3A of FIG. 3.

A dental flossing device was assembled by inserting the stackable dental floss holder of Example 2 into the head portion of the handle of Example 1. The thus-assembled dental flossing device is shown in FIG. 3. The indentations on the dental floss holder receive the protrusions on the head portion of the handle in releasable, frictional engagement. Correspondingly, the indentations on the head portion of the handle receive the protrusions on the dental floss holder in releasable, frictional engagement. The snap fit projections 27A,27B on the arms 22,23 of dental floss holder 20 are engaged with ends 13,15 (including the lower corners of said ends) of the head portion of the handle.

Figure 5:
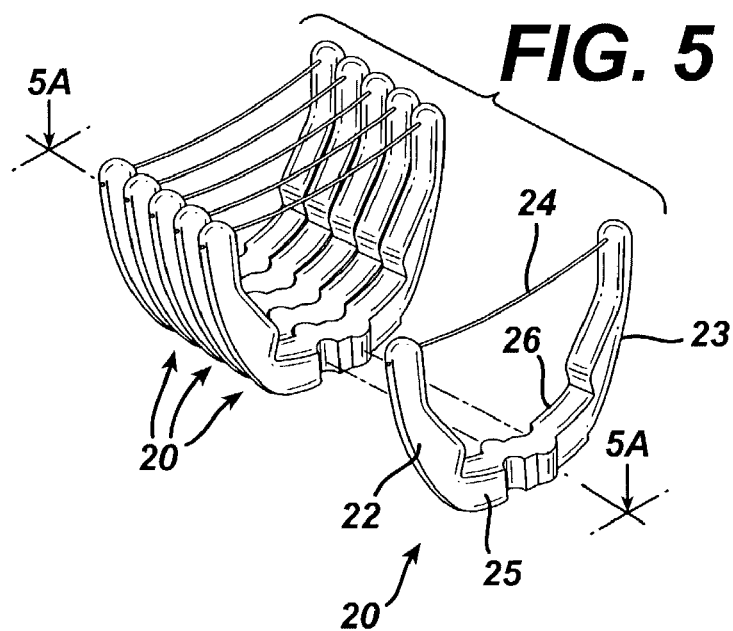
FIG. 5 is a perspective view showing five of the dental floss holders of FIG. 2 in stacked form, with a sixth inch dental floss holder in position to be engaged with said stack.

FIG. 5 shows five of the dental floss holders of FIG. 2 in a stack with a sixth such dental floss holder about to be added to said stack. A stack of the dental floss holders, typically 10 or 20 holders to a stack, can be packaged, e.g., in plastic wrap, a thermoformed container with lid, or the like for subsequent sale.

Figure 5A:
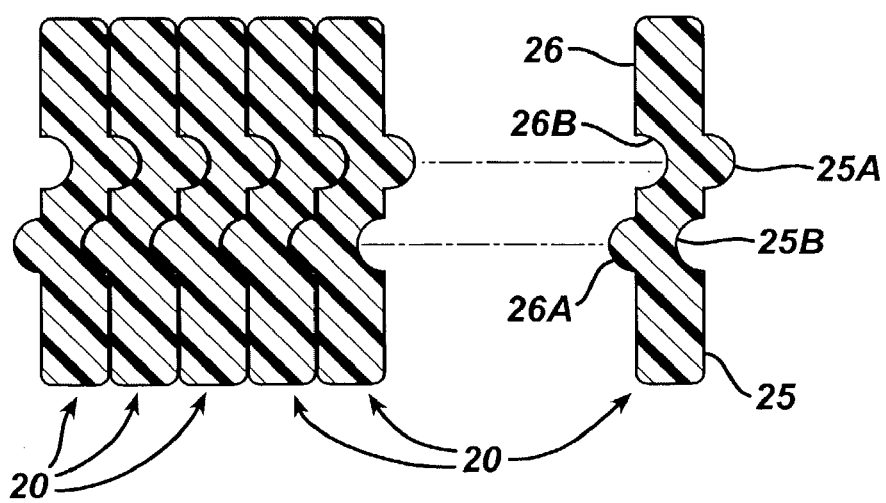
FIG. 5A is a cross-section taken along line 5A—5A of FIG. 5.

FIG. 5a illustrates the manner in which the protrusion and indentation on the base of one dental floss holder (e.g., the right-most holder in the stack of five) will mate with the indentation and protrusion on an adjacent dental floss holder (e.g., the single dental floss holder in FIG. 5a)

What is claimed is:

1. A dental floss holder comprising a base portion integral with and extending between a pair of spaced-apart arms extending from said base portion; a length of dental floss being secured between the distal ends of said arms; said base portion comprising a first lateral side and a second lateral side; each lateral side comprising at least one protrusion and at least one indentation spaced laterally therefrom, wherein each of said arms comprises a snap-fit projection for engagement with ends of a head portion of a handle to which said dental floss holder is to be secured.

2. A dental floss holder according to claim 1 wherein said at least one protrusion on said first lateral side is disposed opposite said at least one indentation on said second lateral side.

3. A dental floss holder according to claim 1 wherein said at least one indentation on said first lateral side is disposed opposite said at least one protrusion on said second lateral side.

4. A dental floss holder according to claim 1 wherein said at least one protrusion on said first lateral side is disposed opposite said at least one indentation on said second lateral side and said at least one indentation on said first lateral side is disposed opposite said at least one protrusion on said second lateral side.

5. A plurality of dental floss holders according to claim 1 in stacked form.

6. A plurality of dental floss holders according to claim 1 in stacked form and packaged.

7. A dental floss holder according to claim 1 which, exclusive of said dental floss, comprises polypropylene.

8. A dental floss holder according to claim 1 wherein said dental floss comprises multifilament yarn of ultra high molecular weight polyethylene.

9. A dental floss holder comprising a base portion integral with and extending between a pair of spaced-apart arms extending from said base portion; a length of dental floss being secured between the distal ends of said arms; said base portion comprising a first lateral side and a second lateral side; each lateral side comprising at least one protrusion and at least one indentation spaced laterally therefrom, wherein said at least one protrusion on said first lateral side is disposed opposite said at least one indentation on said second lateral side and said at least one indentation on said first lateral side is disposed opposite said at least one protrusion on said second lateral side, and wherein each of said arms comprises a snap-fit projection for engagement with ends of a head portion of a handle to which said dental floss holder is to be secured.

10. A plurality of dental floss holders according to claim 9 in stacked form.

11. A plurality of dental floss holders according to claim 9 in stacked form and packaged.

12. A dental floss holder according to claim 9 which, exclusive of said dental floss, comprises polypropylene.

13. A dental floss holder according to claim 9 wherein said dental floss comprises multifilament yarn of ultra high molecular weight polyethylene.

* * * * *